(12) United States Patent
Braun et al.

(10) Patent No.: US 8,148,433 B2
(45) Date of Patent: Apr. 3, 2012

(54) CONCENTRATED INVERSE LATEX, PROCESS FOR PREPARING IT AND INDUSTRIAL USE THEREOF

(75) Inventors: Olivier Braun, Castres (FR); Paul Mallo, Croissy-sur-Seine (FR)

(73) Assignee: Societe d'Exploitation de Produits pour les Industries Chimiques (SEPPIC), Paris (FR)

( * ) Notice: Subject to any disclaimer, the term of this patent is extended or adjusted under 35 U.S.C. 154(b) by 823 days.

(21) Appl. No.: 11/793,268

(22) PCT Filed: Dec. 8, 2005

(86) PCT No.: PCT/FR2005/051058
§ 371 (c)(1),
(2), (4) Date: Dec. 27, 2007

(87) PCT Pub. No.: WO2006/064151
PCT Pub. Date: Jun. 22, 2006

(65) Prior Publication Data
US 2008/0312343 A1    Dec. 18, 2008

(30) Foreign Application Priority Data
Dec. 16, 2004  (FR) ..................................... 04 53017

(51) Int. Cl.
*A61K 47/30*   (2006.01)
*C08L 33/06*   (2006.01)
*C09B 67/00*   (2006.01)

(52) U.S. Cl. ..................................... 514/772.3; 524/560

(58) Field of Classification Search .................... 424/401
See application file for complete search history.

(56) References Cited

U.S. PATENT DOCUMENTS

| 6,107,398 A | 8/2000 | Mallo et al. |
| 7,015,279 B2 * | 3/2006 | Braun et al. ................. 524/815 |
| 7,033,600 B1 * | 4/2006 | Mallo et al. .................. 424/401 |

FOREIGN PATENT DOCUMENTS
EP    0 896 966 A    2/1999

OTHER PUBLICATIONS

WO01/35922. Novel positive latex and use in cosmetics. Inventors: Mallo, Paul; Michel, Nelly. Published May 2001.*

* cited by examiner

*Primary Examiner* — Fereydoun G Sajjadi
*Assistant Examiner* — Audrea Buckley
(74) *Attorney, Agent, or Firm* — Young & Thompson

(57) ABSTRACT

The invention relates to a composition in the form of a positive latex comprising a) between 50 wt. % and 80 wt. % of at least one cross-linked, branched, or linear organic polymer (P), b) between 5 wt. % and 10 wt. % of a water-in-oil (W/O) emulsifying system ($S_1$), c) between 5 wt. % and 45 wt. % of at least one oil, and d) between 0 wt. % and 5 wt. % of water. The inventive composition is characterized in that between 0.01 mol. % and 10 mol. % of the monomeric patterns of said monomer P comprise at least one neutral monomer of formula (I): $C(R_1)(R_3)=C(R_2)-C(=O)-O-(CH_2-CH_2-O)_n-R_4$ (I) wherein the radicals $R_1$, $R_2$ and $R_3$, which are the same or different, independently represent a hydrogen atom or a linear or branched alkyl radical comprising between 1 and 4 carbon atoms, the radical $R_4$ represents a linear or branched, saturated or unsaturated, aliphatic radical comprising between 6 and 30 carbon atoms, and n represents a number between 1 and 50. The invention also relates to a method for the production of said composition and the use of the same.

10 Claims, No Drawings

CONCENTRATED INVERSE LATEX, PROCESS FOR PREPARING IT AND INDUSTRIAL USE THEREOF

The present patent application relates to water-in-oil inverse latices, to a process for preparing them and to their use as thickeners and/or emulsifiers in industrial products, skincare and haircare products or for the manufacture of cosmetic, dermopharmaceutical or pharmaceutical preparations.

Inverse latices of the partially or totally salified acid 2-methyl-2-[(1-oxo-2-propenyl)amino]-1-propane-sulfonic acid (also known as 2-acrylamido-2-methyl-propanesulfonic acid, ATBS or AMPS) and also their cosmetic and/or pharmaceutical use have been the subject of many patent applications. However, the presence of large amounts of water and of oil represents an appreciable drawback in terms of volume, cost and occasionally increased risks and/or toxic effects.

Solutions have thus been developed to increase the concentration of polymers in the final latices, for example by subjecting the reaction medium, at the end of polymerization, to a vacuum distillation step in order to remove a more or less large amount of water and oil. However, this distillation is difficult to implement since it often induces destabilization of the inverse latex, which needs to be countered by the prior addition of stabilizers. European patent applications EP 0 161 038 and EP 0 126 528 and also British patent application GB 1 482 515 disclose such a use of stabilizing polymers.

The drawback of these products is that they contain alcohols or glycols that might induce environmental problems. Furthermore, the reaction medium occasionally sets to a solid during the distillation step, without this phenomenon having ever really been explained, but the definite consequence of which is destruction of the batch of inverse latex and tiresome and expensive cleaning of the reactor. Finally, even when the distillation proceeds correctly, the inverse latices obtained often invert with difficulty, have a high viscosity and occasionally contain microgels. These drawbacks thus prohibit their use in the manufacture of cosmetic formulations and/or in textile printing.

Accordingly, the Applicant set itself the aim of developing concentrated inverse latices, i.e. latices comprising at least 50% by weight of polymer and less than 5% by weight of water, which do not have such drawbacks and which have an improved content of electrolytes.

According to a first aspect, one subject of the invention is a composition in the form of an inverse latex comprising:
a) from 50% by weight to 80% of at least one linear, branched or crosslinked organic polymer (P),
b) from 5% by weight to 10% of an emulsifying system ($S_1$) of water-in-oil (W/O) type,
c) from 5% by weight to 45% by weight of at least one oil, and
d) from 0% to 5% of water,
and characterized in that from 0.01% to 10% in molar proportions of the monomer units that said polymer P comprises is at least one neutral monomer of formula (I):

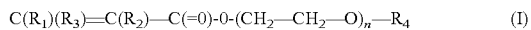

$$C(R_1)(R_3)=C(R_2)-C(=O)-O-(CH_2-CH_2-O)_n-R_4 \quad (I)$$

in which the radicals $R_1$, $R_2$ and $R_3$, which may be identical or different, represent, independently of each other, a hydrogen atom or a linear or branched alkyl radical containing from 1 to 4 carbon atoms, the radical $R_4$ represents a linear or branched, saturated or unsaturated aliphatic radical containing from 6 to 30 carbon atoms and n represents a number between 1 and 50.

The term "linear or branched alkyl radical containing from 1 to 4 carbon atoms" denotes for the radicals $R_1$, $R_2$ and $R_3$ methyl, ethyl, propyl, isopropyl, butyl, isobutyl, sec-butyl or tert-butyl radicals.

The term "linear or branched, saturated or unsaturated aliphatic radical containing from 6 to 30 carbon atoms" denotes for the radical $R_4$ saturated linear radicals more particularly such as, for example, hexyl, octyl, nonyl, decyl, undecyl, dodecyl, tetradecyl, hexadecyl, octadecyl, eicosyl, docosyl, tetracosyl, hexacosyl, octacosyl or triacontyl radicals.

A subject of the invention is more particularly a composition as defined in claim 1, in which from 0.05% to 5% in molar proportions and preferably from 0.1% to 1% in molar proportions of the monomer units that said polymer P comprises is at least one neutral monomer of formula (I).

The composition as defined above contains either a single polymer (P) or a mixture of different polymers (P).

According to a first particular aspect of the present invention, the polymer (P) is:
either a copolymer in which each of the various monomers of the compound of formula (I) is chosen, independently of each other, either from those containing a partially or totally salified strong acid function or from those containing a partially or totally salified weak acid function or from neutral monomers, or from cationic monomers.

In the composition as defined above, the emulsifying system ($S_1$) of water-in-oil (W/O) type consists either of a single surfactant or of a mixture of surfactants on condition that said mixture has an HLB value that is low enough to induce water-in-oil emulsions. Examples of emulsifiers of water-in-oil type include sorbitan esters, for instance sorbitan oleate, for instance the product sold by the company SEPPIC under the name Montane™ 80, sorbitan isostearate, for instance the product sold by the company SEPPIC under the name Montane™ 70 or sorbitan sesquioleate, for instance the product sold by the company SEPPIC under the name Montane™ 83. Mention may also be made of certain polyethoxylated sorbitan esters, for example pentaethoxylated sorbitan monooleate, for instance the product sold by the company SEPPIC under the name Montanox™ 81 or pentaethoxylated sorbitan isostearate, for instance the product sold under the name Montanox™ 71 by the company SEPPIC. Mention may also be made of diethoxylated oleocetyl alcohol, for instance the product sold under the name Simulsol™ OC 72 by the company SEPPIC, polyesters with a molecular weight of between 1000 and 3000, products of condensation between a poly(isobutenyl)succinic acid or the anhydride thereof such as Hypermer™ 2296 sold by the company Uniqema or, finally, block copolymers with a molecular weight of between 2500 and 3500, for instance Hypermer™ B246 sold by the company Uniqema or Simaline™ IE 200 sold by the company SEPPIC.

The term "branched polymer" denotes, for (P), a nonlinear polymer containing pendent chains so as to obtain, when this polymer is dissolved in water, a high state of entanglement leading to very high low-gradient viscosities.

The term "crosslinked polymer" denotes, for (P), a nonlinear polymer having in water a water-insoluble but water-swellable three-dimensional network and thus leading to the production of a chemical gel.

The composition according to the invention may comprise linear polymers, crosslinked polymers and/or branched polymers.

When the polymer (P) is crosslinked, it is more particularly crosslinked with a diethylenic or polyethylenic compound in a molar proportion, expressed relative to the monomers used, of less than or equal to 0.25%, more particularly less than or equal to 0.05% and most particularly between 0.005% and 0.01%. Preferably, the crosslinking agent and/or the branching agent is chosen from ethylene glycol dimethacrylate, diethylene glycol diacrylate, sodium diallyloxyacetate, ethylene glycol diacrylate, diallyl urea, triallylamine, trimethylolpropane triacrylate and methylenebis(acrylamide), or a mixture of these compounds.

The strong acid function of the monomers comprising one is especially the sulfonic acid function or the phosphonic acid function. Said monomers are, for example, partially or totally salified styrenesulfonic acid or, preferably, partially or totally salified 2-methyl-2-[(1-oxo-2-propenyl)amino]-1-propanesulfonic acid (also known as 2-acrylamido-2-methylpropanesulfonic acid).

The weak acid function of monomers comprising one is especially the partially salified carboxylic acid function. Said monomers may be, for example, acrylic acid, methacrylic acid, itaconic acid, maleic acid or partially or totally salified 3-methyl-3-[(1-oxo-2-propenyl)amino]butanoic acid.

For the monomers with a strong acid function or with a weak acid function, the term "salified" indicates that they are alkali metal salts such as the sodium or potassium salts, salts of nitrogenous bases, for instance the ammonium salt, the lysine salt or the monoethanolamine ($HO-CH_2-CH_2-NH_4^+$) salt.

The various neutral monomers of the compound of formula (I) are especially chosen from acrylamide, methacrylamide, diacetoneacrylamide, dimethyl-acrylamide, N-isopropylacrylamide, N-[2-hydroxy-1,1-bis(hydroxymethyl)ethyl] propenamide [or tris(hydroxymethyl)acrylamidomethane or N-tris(hydroxymethyl)methylacrylamide, also known as THAM], (2-hydroxyethyl)acrylate, (2,3-dihydroxypropyl)acrylate, (2-hydroxyethyl)methacrylate, (2,3-dihydroxypropyl)methacrylate, an ethoxylated derivative with a molecular weight of between 400 and 1000, of each of these esters, or vinylpyrrolidone.

The cationic monomers are especially chosen from quaternary ammonium derivatives. Said monomers may be, for example, the salts of 2,N,N,N-tetramethyl-2-[(1-oxo-2-propenyl)amino]propanammonium, of 2,N,N-tri-methyl-2-[(1-oxo-2-propenyl)amino]propanammonium, of N,N,N-trimethyl-2-[(1-oxo-2-propenyl)oxy]ethanammonium, of N,N,N-trimethyl-3-[(1-oxo-2-propenyl)oxy]propan-ammonium, of N,N,N-trimethyl-2-[(1-oxo-2-propenyl)-amino]propan-ammonium or of diallyldimethylammonium. The term "salt" more particularly means the chlorides, bromides or iodides of said ammonium salts.

A subject of the invention is, more particularly, a composition as defined above for which, in formula (I), the radical $R_4$ represents a linear or branched, saturated or unsaturated aliphatic radical containing from 8 to 24 carbon atoms, a composition as defined above for which, in formula (I), the radicals $R_1$, $R_2$ and $R_3$, which may be identical or different, represent, independently of each other, a hydrogen atom or a methyl radical, and a composition as defined above for which, in formula (I), n is a number between 1 and 30 and preferably a number between 1 and 25.

According to another particular aspect, in the composition as defined above, the monomer is chosen from the compounds of formula (I'):

$$CH_2=CH-C(=O)-O-(CH_2-CH_2-O)_{n'}-R'_4 \qquad (I')$$

corresponding to formula (I) in which the radicals $R_1$, $R_2$ and $R_3$ each represent a hydrogen atom, the radical $R_4$ represents an aliphatic radical chosen from octyl, decyl, dodecyl, tetradecyl, hexadecyl, octadecyl, eicosyl, docosyl and tetracosyl radicals, and n' represents a number between 4 and 25; or alternatively the compounds of formula (I"):

$$CH_2=C(CH_3)-C(=O)-O-(CH_2-CH_2-O)_{n''}-R''_4 \qquad (I'')$$

corresponding to formula (I) in which the radicals $R_1$ and $R_3$ each represent a hydrogen atom, the radical $R_2$ represents a methyl group, the radical $R_4$ represents an aliphatic radical chosen from octyl, dodecyl, tetradecyl, hexadecyl, octadecyl, eicosyl, docosyl and tetracosyl radicals, and n' represents a number between 4 and 25.

The polymer (P) is then preferably chosen from:
crosslinked copolymers of acrylic acid partially salified in the form of the sodium salt or of the ammonium salt, of acrylamide and of tetraethoxylated lauryl acrylate;
crosslinked copolymers of 2-methyl-2-[(1-oxo-2-propenyl)amino]-1-propanesulfonic acid partially salified in the form of the sodium salt, of acrylamide and of tetraethoxylated lauryl acryate;
crosslinked copolymers of 2-methyl-2-[(1-oxo-2-propenyl)amino]-1-propanesulfonic acid and of acrylic acid, which are partially salified in the form of the sodium salt, and of tetraethoxylated lauryl acrylate;
crosslinked copolymers of 2-methyl-2-[(1-oxo-2-propenyl)amino]-1-propanesulfonic acid partially salified in the form of the sodium salt, of 2-hydroxyethyl acrylate and of tetraethoxylated lauryl acrylate;
crosslinked copolymers of N,N,N-trimethyl-3-(1-oxo-2-propenyl)propanammonium acrylamide and of tetraethoxylated lauryl acrylate;
crosslinked copolymers of 2-methyl-2-[(1-oxo-2-propenyl)amino]-1-propanesulfonic acid partially salified in the form of the sodium salt, and of tetraethoxylated lauryl acrylate;
crosslinked copolymers of acrylic acid partially salified in the form of the ammonium salt or of the monoethanolamine salt, and of tetraethoxylated lauryl acrylate;
copolymers of acrylamide, of N,N,N-trimethyl-3-(1-oxo-2-propenyl)propanammonium, of tris(hydroxy-methyl)aminomethylacrylamide and of tetraethoxylated lauryl acrylate;
crosslinked copolymers of acrylamide, of 2-methyl-2-[(1-oxo-2-propenyl)amino]-1-propanesulfonic acid and of acrylic acid, which are partially salified in the form of the sodium salt, and of tetraethoxylated lauryl acrylate; and
copolymers of 2-methyl-2-[(1-oxo-2-propenyl)-amino]-1-propanesulfonic acid partially salified in the form of the sodium salt, of acrylamide, of vinyl-pyrrolidone and of tetraethoxylated lauryl acrylate.

According to another particular mode of the present invention, the composition as defined above comprises at least 60% by weight and not more than 70% by weight of polymer (P).

According to another particular mode of the present invention, the composition as defined above also comprises up to 5% of its weight of an emulsifying system ($S_2$) of oil-in-water (O/W) type.

The expression "emulsifier of the oil-in-water type" denotes emulsifiers with an HLB value that is high enough to give oil-in-water emulsions such as ethoxylated sorbitan esters, for instance sorbitan oleate polyethoxylated with 20 mol of ethylene oxide, sold by the company SEPPIC under the name Montanox™ 80, sorbitan laurate polyethoxylated with 20 mol of ethylene oxide, sold by the company SEPPIC under the name Montanox™ 20, castor oil polyethoxylated with 40 mol of ethylene oxide, sold under the name Simulsol™ OL50, decaethoxylated oleodecyl alcohol sold by the company SEPPIC under the name Simulsol™ OC 710, heptaethoxylated lauryl alcohol sold under the name Simulsol™ P7, decaethoxylated nonylphenol sold by the company SEPPIC under the name Nonarox™-10-30 or polyethoxylated sorbitan hexaoleates sold by the company SEPPIC under the name Simaline™-IE 400.

In the composition that is the subject of the present invention, the oil phase consists either of a commercial mineral oil containing saturated hydrocarbons, for instance paraffins, isoparaffins or cycloparaffins having at room temperature a density of between 0.7 and 0.9 and a boiling point of greater than about 250° C., for instance Marcol™ 52 sold by Exxon Chemical, or of a plant oil, for instance squalane of plant origin, or a synthetic oil such as hydrogenated polyisobutene or hydrogenated polydecene, or of a mixture of several of these oils. Marcol™ 52 is a commercial oil corresponding to the definition of liquid petroleum jellies of the French Codex. It is a white mineral oil in accordance with the FDA regulations CFR 172.878 and CFR 178.3620 (a) and is registered in the US Pharmacopea, US XXIII (1995) and in the European Pharmacopea (1993). The composition according to the invention may also contain various additives such as complexing agents, transfer agents or chain-limiting agents.

According to another aspect of the present invention, a subject thereof is a process for preparing the composition as defined above, characterized in that:
a) an aqueous phase (A) containing the monomers and the optional hydrophilic additives is emulsified in an organic phase (O) containing the surfactant system ($S_1$), a mixture consisting of the oil intended to be present in the final composition and of a volatile oil and the optional hydrophobic additives,
b) the polymerization reaction is initiated by introduction into the emulsion formed in a) of a free-radical initiator, and the reaction is then left to proceed, and
c) the reaction medium obtained from step b) is concentrated by distillation until said volatile oil has been completely removed.

The volatile oils that are suitable for use in the process as defined above are, for example, light isoparaffins containing from 8 to 11 carbon atoms, for instance those sold under the names Isopar™ G, Isopar™ L, Isopar™ H or Isopar™ J.

According to one preferred implementation of the process as defined above, the polymerization reaction is initiated with a redox couple, such as the cumene hydroperoxide-sodium metabisulfite couple, at a temperature of less than or equal to 10° C., and is then performed either quasi-adiabatically up to a temperature of greater than or equal to 40° C. and more particularly greater than or equal to 50° C., or by controlling the temperature change.

When step c) is complete, one or more emulsifiers of oil-in-water type are introduced, if desired, at a temperature below 50° C.

A subject of the invention is also the use of the composition as defined above for preparing a cosmetic, dermopharmaceutical or pharmaceutical topical composition.

A topical composition according to the invention, intended to be applied to human or animal skin or mucous membranes, may consist of a topical emulsion comprising at least one aqueous phase and at least one oil phase. This topical emulsion may be of the oil-in-water type. More particularly, this topical emulsion may consist of a fluid emulsion, such as a milk or a fluid gel. The oil phase of the topical emulsion may consist of a mixture of one or more oils.

A topical composition according to the invention may be intended for cosmetic use or may be used for preparing a medicament intended for treating skin and mucous membrane diseases. In the latter case, the topical composition then comprises an active principle that may consist, for example, of an anti-inflammatory agent, a muscle relaxant, an antifungal agent or an antibacterial agent.

When the topical composition is used as a cosmetic composition intended to be applied to the skin or mucous membranes, it may or may not comprise an active principle, for example a moisturizer, a tanning agent, a sunscreen, an anti-wrinkle agent, an agent for slimming purposes, a free-radical scavenger, an antiacne agent or an antifungal agent.

A topical composition according to the invention usually comprises between 0.1% and 10% by weight of the thickener defined above. The pH of the topical composition is preferably greater than or equal to 5.

The topical composition may also comprise compounds conventionally included in compositions of this type, for instance fragrances, preserving agents, dyes, emollients or surfactants.

According to yet another aspect, the invention relates to the use of the novel thickener in accordance with the invention, mentioned above, for thickening and emulsifying a topical composition comprising at least one aqueous phase.

The composition according to the invention is an advantageous substitute for those sold under the names Sepigel™ T 305, Sepigel™ 501, Sepigel™ EG, Sepigel™ NS or Sepigel™ 600 by the Applicant, since it also has good compatibility with the other excipients used for the preparation of formulations such as milks, lotions, creams, soaps, baths, balms, shampoos or hair conditioners. It may also be used with said Sepigel or Simulgel products.

It is especially compatible with the concentrates described and claimed in international publications WO 92/06778, WO 95/04592, WO 95/13863, WO 96/37285, WO 98/22207 and WO 98/47610 and in patent FR 2 734 496, with the surfactants described in WO 93/08204.

It is particularly compatible with Montanov™ 68, Montanov™ 82, Montanov™ 202 or Sepiperl™ N. It may also be used in emulsions of the type such as those described and claimed in EP 0 629 396 and in cosmetically or physiologically acceptable aqueous dispersions with an organopolysiloxane compound chosen, for example, from those described in WO 93/05762 or in WO 93/21316.

It may also be used to form aqueous gels at cosmetically or physiologically acceptable acidic pH, such as those described in WO 93/07856; it may also be used in combination with nonionic celluloses, to form, for example, styling gels such as those described in EP 0 684 024, or alternatively in combination with fatty acid esters of sugars, to form compositions for treating the hair or the skin such as those described in EP 0 603 019, or alternatively in shampoos or hair conditioners as described and claimed in WO 96/21316 or, finally, in combination with an anionic homopolymer such as Carbopol™ to form hair-treatment products such as those described in DE 195 23 596, or in combination with other thickening polymers.

The composition according to the invention is also compatible with active principles such as, for example, self-tanning agents, for instance dihydroxyacetone (DHA) or anti-acne agents; it may thus be introduced into self-tanning compositions such as those claimed in EP 0 715 845, EP 0 604 249, EP 0 576 188 or in WO 93/07902.

It is also compatible with N-acylamino acid derivatives, which allows its use in calmative compositions, especially for sensitive skin, such as those described or claimed in WO 92/21318, WO 94/27561 or in WO 98/09611.

When the composition as defined above is intended for treating the hair, it more particularly comprises an inverse latex of cationic polymer that is a subject of the present invention.

When the composition as defined above is intended for treating the skin and/or mucous membranes, it more particularly comprises an inverse latex of anionic polymer that is a subject of the present invention.

The inverse latices that are subjects of the present invention may be used as thickeners for textile printing pastes.

The examples that follow are aimed at illustrating the present invention.

EXAMPLE 1

Inverse Latex of the Copolymer AM/AA/(ALE-4OE) Crosslinked with MBA (Anionic Thickener—Composition 1)

a) —The following are successively introduced into a first beaker, with stirring:
  106.5 g of a commercial 50% (by mass) acrylamide (AM) solution,
  162.0 g of glacial acrylic acid (AA),
  98.1 g of an aqueous ammonia solution at 29.3% by weight,
  0.047 g of methylenebis(acrylamide) (MBA),
  0.45 g of a commercial 40% sodium diethylenetriaminepentaacetate solution,
  deionized water, to make up to 680 g.
b) —An organic phase is prepared in a second beaker by mixing together the following:
  121 g of polyisobutene,
  28 g of Marcol™ 52,
  99 g of Isopar™ H,
  17 g of Montane™ 70,
  3 g of Hypermer™ 2296,
  5 g of Simaline™ IE 200,
  1.2 g of tetraethoxylated lauryl acrylate (commercial) (ALE-4OE),
  0.1 g of AIBN.
c) —The aqueous phase is then introduced into the organic phase with stirring and the pre-emulsion thus obtained is then subjected to vigorous mechanical stirring using a turbomixer of Silverson type so as to create a fine emulsion under a nitrogen sparge.
d) —After cooling to about 8° C., the polymerization reaction is initiated using the redox couple: cumene hydroperoxide/sodium metabisulfite.
e) —Once the polymerization reaction is complete, the Isopar™ H and virtually all of the water are removed by vacuum distillation.
f) —After introduction of 2% of Montanox™ 20 and 4% of Laureth-7, an anionic thickening inverse latex containing about 63% polymer is obtained. The product obtained is sparingly viscous, it has high thickening power and it inverts easily. Its water content measured by Karl-Fisher titrimetry is 1.8% by weight.

Viscosity Measurements (Brookfield RVT Viscometer)
  A—The viscosities of an aqueous solution comprising 2% by weight of the concentrated inverse latex obtained and of aqueous solutions containing 2% by weight of said inverse latex and 0.1%, 1% and 5% by weight of sodium chloride are measured.

| | Spindle (S): spindle spin speed (V) (in rpm) | Viscosity in mPa · s |
|---|---|---|
| Inverse latex | | |
| Aqueous solution at 2% by weight | S 6, 5 rpm | 79 400 |
| Aqueous solution at 2% by weight + 0.1% by weight of NaCl | S 6, 5 rpm | 45 200 |
| Aqueous solution at 2% by weight + 1% by weight of NaCl | S 3, 5 rpm | 3300 |
| Aqueous solution at 2% by weight + 5% by weight of NaCl | S 3, 5 rpm | nd | nd: not determined

EXAMPLE 2

Inverse Latex of the Copolymer AM/AA/(ALE-4OE) Crosslinked with MBA (Anionic Thickener—Composition 2)

a) —The following are successively introduced into a first beaker, with stirring:
  106.5 g of a commercial 50% (by mass) acrylamide (AM) solution,
  162.0 g of glacial acrylic acid (AA),
  98.1 g of an aqueous ammonia solution at 29.3% by weight,
  0.047 g of methylenebis(acrylamide) (MBA),
  0.45 g of a commercial 40% sodium diethylenetriaminepentaacetate solution,
  deionized water, to make up to 680 g.
b) —An organic phase is prepared in a second beaker by mixing together the following:
  121 g of polyisobutene,
  28 g of Marcol™ 52,
  99 g of Isopar™ H,
  17 g of Montane™ 70,
  3 g of Hypermer™ 2296,
  5 g of Simaline™ IE 200,
  3.0 g of tetraethoxylated lauryl acrylate (commercial) (ALE-4OE),
  0.1 g of AIBN.
c) —The aqueous phase is then introduced into the organic phase with stirring and the pre-emulsion thus obtained is then subjected to vigorous mechanical stirring using a turbomixer of Silverson type so as to create a fine emulsion under a nitrogen sparge.
d) —After cooling to about 8° C., the polymerization reaction is initiated using the redox couple: cumene hydroperoxide/sodium metabisulfite.
e) —Once the polymerization reaction is complete, the Isopar™ H and virtually all of the water are removed by vacuum distillation.
f) —After introduction of 2% of Montanox™ 20 and 4% of Laureth-7, an anionic thickening inverse latex containing about 63% polymer is obtained. The product obtained is sparingly viscous, it has high thickening power and it inverts easily. Its water content measured by Karl-Fisher titrimetry is 2% by weight.

Viscosity Measurements (Brookfield RVT Viscometer)

A—The viscosities of an aqueous solution comprising 2% by weight of the concentrated inverse latex obtained and of aqueous solutions containing 2% by weight of said inverse latex and 0.1%, 1% and 5% by weight of sodium chloride are measured.

| | Spindle (S): spindle spin speed (V) (in rpm) | Viscosity in mPa · s |
|---|---|---|
| Inverse latex Aqueous solution at 2% by weight | S 6, 5 rpm | 74 600 |
| Aqueous solution at 2% by weight + 0.1% by weight of NaCl | S 6, 5 rpm | 43 600 |
| Aqueous solution at 2% by weight + 1% by weight of NaCl | S 3, 5 rpm | 6060 |
| Aqueous solution at 2% by weight + 5% by weight of NaCl | S 3, 5 rpm | nd | nd: not determined

EXAMPLE 3

Inverse Latex of the Copolymer AM/AA/(ALE-4OE) (Anionic Thickener—Composition 3)

The process is performed as in the preceding example, but in this case 6 g of tetraethoxylated lauryl acrylate are used and no methylenebisacrylamide is introduced.

After introduction of 2% of Montanox™ 20 and 4% of Laureth-7, an anionic thickening inverse latex containing about 63% polymer is obtained. The product obtained is sparingly viscous, it has high thickening power and it inverts easily. Its water content measured by Karl-Fisher titrimetry is 2.3% by weight.

Viscosity Measurements (Brookfield RVT Viscometer)

A—The viscosities of an aqueous solution comprising 2% by weight of the concentrated inverse latex obtained and of aqueous solutions containing 2% by weight of said inverse latex and 0.1%, 1% and 5% by weight of sodium chloride are measured.

| | Spindle (S): spindle spin speed (V) (in rpm) | Viscosity in mPa · s |
|---|---|---|
| Inverse latex Aqueous solution at 2% by weight | S 6, 5 rpm | 37 000 |
| Aqueous solution at 2% by weight + 0.1% by weight of NaCl | S 6, 5 rpm | 26 800 |
| Aqueous solution at 2% by weight + 1% by weight of NaCl | S 3, 5 rpm | 12 100 |
| Aqueous solution at 2% by weight + 5% by weight of NaCl | S 3, 5 rpm | 7300 |

EXAMPLE 4

Inverse Latex of the Copolymer AM/AA/(ALE-4OE) Crosslinked with MBA (Anionic Thickener—Composition 4)

The process is performed as previously, but using 6 g of tetraethoxylated lauryl acrylate (commercial) (ALE-4OE) and 0.012 g of methylenebis(acrylamide) (MBA).

f)—After introduction of 2% of Montanox™ 20 and 4% of Laureth-7, an anionic thickening inverse latex containing about 63% polymer is obtained. The product obtained is sparingly viscous, it has high thickening power and it inverts easily. Its water content measured by Karl-Fisher titrimetry is 2.2% by weight.

Viscosity Measurements (Brookfield RVT Viscometer)

A—The viscosities of an aqueous solution comprising 2% by weight of the concentrated inverse latex obtained and of aqueous solutions containing 2% by weight of said inverse latex and 0.1%, 1% and 5% by weight of sodium chloride are measured.

| | Spindle (S): spindle spin speed (V) (in rpm) | Viscosity in mPa · s |
|---|---|---|
| Inverse latex Aqueous solution at 2% by weight | S 6, 5 rpm | 75 000 |
| Aqueous solution at 2% by weight + 0.1% by weight of NaCl | S 6, 5 rpm | 52 400 |
| Aqueous solution at 2% by weight + 1% by weight of NaCl | S 3, 5 rpm | 13 700 |
| Aqueous solution at 2% by weight + 5% by weight of NaCl | S 3, 5 rpm | 3000 |

EXAMPLE 5

Inverse Latex of the Copolymer AM/AA/(ALE-4OE) Crosslinked with MBA (Anionic Thickener—Composition 5)

The process is performed as previously, but introducing 1.2 g of tetraethoxylated lauryl acrylate (commercial) (ALE-4OE) and 0.14 g of methylenebis(acrylamide) (MBA).

After introduction of 2% of Montanox™ 20 and 4% of Laureth-7, an anionic thickening inverse latex containing about 63% polymer is obtained. The product obtained is sparingly viscous, it has high thickening power and it inverts easily. Its water content measured by Karl-Fisher titrimetry is 2.8% by weight.

Viscosity Measurements (Brookfield RVT Viscometer)

A—The viscosities of an aqueous solution comprising 2% by weight of the concentrated inverse latex obtained and of aqueous solutions containing 2% by weight of said inverse latex and 0.1%, 1% and 5% by weight of sodium chloride are measured.

| | Spindle (S): spindle spin speed (V) (in rpm) | Viscosity in mPa·s |
|---|---|---|
| Inverse latex Aqueous solution at 2% by weight | S 6; 5 rpm | 160 000 |
| Aqueous solution at 2% by weight + 0.1% by weight of NaCl | S 6; 5 rpm | 80 600 |
| Aqueous solution at 2% by weight + 1% by weight of NaCl | S 3; 5 rpm | 1 000 |
| Aqueous solution at 2% by weight + 5% by weight of NaCl | S 3; 5 rpm | nd | nd: not determined

EXAMPLE 6

Inverse Latex of the Terpolymer AM/ATBS/AA/(ALE-4OE) (Anionic Thickener—Composition 6)

a) The following are successively introduced into a first reactor, with stirring:
  227.5 kg of a commercial 50% (by mass) acrylamide (AM) solution,
  308.1 kg of a commercial 55% solution of the sodium salt of 2-acrylamido-2-methylpropanesulfonic acid (ATBS),
  8.8 kg of acrylic acid (AA),
  0.032 kg of methylenebis(acrylamide) (MBA),
  0.37 kg of a commercial 40% sodium diethylenetri-aminepentaacetate solution,
  the pH is adjusted to 6.2 with sodium hydroxide;
  deionized water so as to bring the total mass to 564.3 kg.
b) —An organic phase is prepared in a second reactor by mixing together:
  107.6 kg of polyisobutene,
  25 kg of Marcol™ 52,
  74.5 kg of Isopar™ H,
  14.1 kg of Montane™ 70,
  2.5 kg of Hypermer™ 2296,
  4.1 kg of Simaline™ IE 200,
  4.8 kg of tetraethoxylated lauryl acrylate,
c) —The aqueous phase is then introduced into the organic phase with stirring and the pre-emulsion thus obtained is then subjected to vigorous mechanical stirring using a turbomixer of Silverson type so as to create a fine emulsion under a nitrogen sparge.
d) —After cooling to about 8° C., the polymerization reaction is initiated with the redox couple: ammonium persulfate/sodium metabisulfite.
e) —Once the polymerization reaction is complete, the Isopar™ G and virtually all of the water are removed by vacuum distillation.
f) —After introducing 5% of Montanox™ 20, an anionic thickening inverse latex containing about 63% polymer is obtained. The product obtained is sparingly viscous, it has high thickening power and it inverts easily. Its water content measured by Karl-Fisher titrimetry is 3.1% by weight.

Viscosity Measurements (Brookfield RVT Viscometer)

| | Spindle (S): spindle spin speed (V) (in rpm) | Viscosity in mPa·s |
|---|---|---|
| Inverse latex | S 4; V: 20 | 1450 |
| Aqueous solution at 2% by weight | S 6; V: 5 | 120 000 |
| Aqueous solution at 2% by weight + 0.1% by weight of NaCl | S 6; V: 5 | 34 000 |

EXAMPLE 7

Inverse Latex of the Terpolymer AA/ATBS/ALE 4OE Crosslinked with MBA (Composition 7)

a) —The following are successively introduced into a first beaker, with stirring:
  560 g of a commercial 55% (by mass) solution of the sodium salt of 2-acrylamido-2-methylpropane-sulfonic acid (ATBSNa)
  73.3 g of glacial acrylic acid solution
  40.6 g of aqueous 50% sodium hydroxide solution
  0.073 g of methylenebis(acrylamide) (MBA)
  0.45 g of a commercial 40% sodium diethylene-tri-aminepentaacetate solution
  the pH is adjusted to 5.0 with 2-acrylamido-2-methyl-propanesulfonic acid powder
  deionized water so as to bring the total mass to 682 g.
b) —An organic phase is prepared in a second reactor by mixing together:
  130 g of polyisobutene,
  30 g of Marcol™ 52,
  90 g of Isopar™ H,
  17 g of Montane™ 70,
  3.0 g of Hypermer™ 2296,
  5.0 g of Simaline™ IE 200,
  9.5 g of tetraethoxylated lauryl acrylate
c) —The aqueous phase is then introduced into the organic phase with stirring and the pre-emulsion thus obtained is then subjected to vigorous mechanical stirring using a turbomixer of Silverson type so as to create a fine emulsion under a nitrogen sparge.
d) —After cooling to about 8° C., the polymerization reaction is initiated with the redox couple: ammonium persulfate/sodium metabisulfite.
e) —Once the polymerization reaction is complete, the Isopar™ H and virtually all of the water are removed by vacuum distillation.
f) —After introducing 2% of Montanox™ 20 and 4% of Laureth-7, an anionic thickening inverse latex containing about 63% polymer is obtained. The product obtained is sparingly viscous, it has high thickening power and it inverts easily. Its water content measured by Karl-Fisher titrimetry is 4% by weight.

Viscosity Measurements (Brookfield RVT Viscometer)

|  | Spindle (S): spindle spin speed (V) (in rpm) | Viscosity in mPa·s |
|---|---|---|
| Inverse latex | S 4; V: 20 | 4000 |
| Aqueous solution at 2% by weight | S 6; V: 5 | 94 000 |
| Aqueous solution at 2% by weight + 0.1% by weight of NaCl | S 6; V: 5 | 38 600 |
| Aqueous solution at 2% by weight + 1% by weight of NaCl | S 3; 5 rpm | 5100 |
| Aqueous solution at 2% by weight + 5% by weight of NaCl | S 3; 5 rpm | 180 |

EXAMPLE 8

Inverse Latex of the Terpolymer AM/AA/(MAS-20 OE) Crosslinked with MBA (Composition 8)

The process is performed as in Example 1, but using 3.4 g of stearyl methacrylate ethoxylated with 20 mol (MAS-20 OE) and 0.034 g of methylenebisacrylamide. A thickening inverse latex whose performance qualities are collated below is thus obtained.

|  | Spindle (S): spindle spin speed (V) (in rpm) | Viscosity in mPa·s |
|---|---|---|
| Inverse latex |  |  |
| Aqueous solution at 2% by weight | S 6; 5 rpm | 87 000 |
| Aqueous solution at 2% by weight + 0.1% by weight of NaCl | S 6; 5 rpm | 49 800 |
| Aqueous solution at 2% by weight + 1% by weight of NaCl | S 3; 5 rpm | 2600 |
| Aqueous solution at 2% by weight + 5% by weight of NaCl | S 3; 5 rpm | 120 |

EXAMPLE 9

Inverse Latex of the Copolymer AM/AA (MBE-25 OE) Crosslinked with MBA (Composition 9)

The process is performed as in Example 8, but using 3.3 g of behenyl methacrylate ethoxylated with 25 mol of ethyleneoxide (MBE-25 OE) instead of the MAS-20 OE.

|  | Spindle (S): spindle spin speed (V) (in rpm) | Viscosity in mPa·s |
|---|---|---|
| Inverse latex |  |  |
| Aqueous solution at 2% by weight | S 6; 5 rpm | 70 000 |
| Aqueous solution at 2% by weight + 0.1% by weight of NaCl | S 6; 5 rpm | 42 400 |

Examples of Cosmetic Formulations

EXAMPLE 10

Care Cream

| Dow Corning ™ 345: | 10% |
|---|---|
| composition 2: | 0.8% |
| Montanov ™ 68: | 4.5% |
| preserving agent: | 0.65% |
| lysine: | 0.025% |
| EDTA (disodium salt): | 0.05% |
| Keltrol ™ T: | 0.2% |
| glycerol: | 3% |
| water: | qs 100% |

EXAMPLE 11

Care Cream

| Dow Corning ™ 345: | 10% |
|---|---|
| composition 4: | 0.8% |
| Montanov ™ 68: | 4.5% |
| perfluoropolymethyl isopropyl ether: | 0.5% |
| preserving agent: | 0.65% |
| lysine: | 0.025% |
| EDTA (disodium salt): | 0.05% |
| Pemulen ™ TR: | 0.2% |
| glycerol: | 3% |
| water: | qs 100% |

EXAMPLE 12

Aftershave Balm

Formula

| A | composition 3: | 1.5% |
|---|---|---|
|  | water: | qs 100% |
| B | Micropearl ™ M100: | 5.0% |
|  | Sepicide ™ CI: | 0.50% |
|  | fragrance: | 0.20% |
|  | 95° ethanol: | 10.0% |

Procedure

Add B to A

EXAMPLE 13

Satin Body Emulsion

Formula

| | | |
|---|---|---|
| A | Simulsol ™ 165: | 5.0% |
| | Lanol ™ 1688: | 8.50% |
| | shea butter: | 2% |
| | liquid paraffin: | 6.5% |
| | Lanol ™ 14 M: | 3% |
| | Lanol ™ S: | 0.6% |
| B | water: | 66.2% |
| C | Micropearl ™ M100: | 5% |
| D | composition 5: | 3% |
| E | Sepicide ™ CI: | 0.3% |
| | Sepicide ™ HB: | 0.5% |
| | Monteine ™ CA: | 1% |
| | fragrance: | 0.20% |
| | vitamin E acetate: | 0.20% |
| | sodium pyrrolidinonecarboxylate: | 1% (moisturizer) |

Procedure

Add C to B, emulsify B in A at 70° C., then add D at 60° C. and then E at 30° C.

EXAMPLE 14

Body Milk

Formula

| | | |
|---|---|---|
| A | Simulsol ™ 165: | 5.0% |
| | Lanol ™ 1688: | 12.0% |
| | Lanol ™ 14 M: | 2.0% |
| | cetyl alcohol: | 0.3% |
| | Schercemol ™ OP: | 3% |
| B | water: | qs 100% |
| C | composition 4: | 0.35% |
| D | Sepicide ™ CI: | 0.2% |
| | Sepicide ™ HB: | 0.5% |
| | fragrance: | 0.20% |

Procedure

Emulsify B in A at about 75° C.; add C at about 60° C. and then D at about 30° C.

EXAMPLE 15

O/W Cream

Formula

| | | |
|---|---|---|
| A | Simulsol ™ 165: | 5.0% |
| | Lanol ™ 1688: | 20.0% |
| | Lanol ™ P: | 1.0% |
| B | water: | qs 100% |
| C | composition 2: | 2.50% |
| D | Sepicide ™ CI: | 0.20% |
| | Sepicide ™ HB: | 0.30% |

Procedure

Introduce B into A at about 75° C.; add C at about 60° C., then D at about 45° C.

EXAMPLE 16

Nongreasy Antisun Gel

Formula

| | | |
|---|---|---|
| A | composition 5: | 3.00% |
| | water: | 30% |
| B | Sepicide ™ C: | 0.20% |
| | Sepicide ™ HB: | 0.30% |
| | fragrance: | 0.10% |
| C | dye: | qs |
| | water: | 30% |
| D | Micropearl ™ M100: | 3.00% |
| | water: | qs 100% |
| E | silicone oil: | 2.0% |
| | Parsol ™ MCX: | 5.00% |

Procedure

Introduce B into A; add C, then D, then E.

EXAMPLE 17

Antisun Milk

Formula

| | | |
|---|---|---|
| A | Sepiperl ™ N: | 3.0% |
| | sesameseed oil: | 5.0% |
| | Parsol ™ MCX: | 5.0% |
| | λ-Carrageenan: | 0.10% |
| B | water: | qs 100% |
| C | composition 3: | 0.80% |
| D | fragrance: | qs |
| | preserving agent: | qs |

Procedure

Emulsify B in A at 75° C., then add C at about 60° C., then D at about 30° C. and adjust the pH if necessary.

EXAMPLE 18

Massage Gel

Formula

| | | |
|---|---|---|
| A | composition 2: | 3.5% |
| | water: | 20.0% |
| B | dye: | 2 drops/100 g |
| | water: | qs |
| C | alcohol: | 10% |
| | menthol: | 0.10% |
| D | silicone oil: | 5.0% |

Procedure

Add B to A; then add C to the mixture, then D.

EXAMPLE 19

Massage Care Gel

Formula

| A | composition 3: | 3.00% |
| --- | --- | --- |
|  | water: | 30% |
| B | Sepicide ™ CI: | 0.20% |
|  | Sepicide ™ HB: | 0.30% |
|  | fragrance: | 0.05% |
| C | dye: | qs |
|  | water: | qs 100% |
| D | Micropearl ™ SQL: | 5.0% |
|  | Lanol ™ 1688: | 2% |

Procedure

Prepare A; add B, then C, then D.

EXAMPLE 20

Radiance Gel

Formula

| A | composition 4: | 4% |
| --- | --- | --- |
|  | water: | 30% |
| B | Elastin HPM: | 5.0% |
| C | Micropearl ™ M100: | 3% |
|  | water: | 5% |
| D | Sepicide ™ CI: | 0.2% |
|  | Sepicide ™ HB: | 0.3% |
|  | fragrance: | 0.06% |
|  | 50% sodium pyrrolidinonecarboxylate: | 1% |
|  | water: | qs 100% |

Procedure

Prepare A; add B, then C, then D.

EXAMPLE 21

Body Milk

Formula

| A | Sepiperl ™ N: | 3.0% |
| --- | --- | --- |
|  | glyceryl triheptanate: | 10.0% |
| B | water: | qs 100% |
| C | composition 5: | 1.0% |
| D | fragrance: | qs |
|  | preserving agent: | qs |

Procedure

Melt A at about 75° C. Emulsify B in A at 75° C. then add C at about 60° C., then D.

EXAMPLE 22

Makeup-Removing Emulsion with Sweet Almond Oil

Formula

| Montanov ™ 68: | 5% |
| --- | --- |
| sweet almond oil: | 5% |
| water: | qs 100% |
| composition 4: | 0.3% |
| glycerol: | 5% |
| preserving agent: | 0.2% |
| fragrance: | 0.3% |

EXAMPLE 23

Moisturizing Cream for Greasy Skin

Formula

| Montanov ™ 68: | 5% |
| --- | --- |
| cetylstearyl octanoate: | 8% |
| octyl palmitate: | 2% |
| water: | qs 100% |
| composition 3: | 0.6% |
| Micropearl ™ M100: | 3.0% |
| mucopolysaccharides: | 5% |
| Sepicide ™ HB: | 0.8% |
| fragrance: | 0.3% |

EXAMPLE 24

Alcohol-Free Soothing Aftershave Balm

Formula

| mixture of lauryl amino acids: | 0.1% to 5% |
| --- | --- |
| magnesium potassium aspartate: | 0.002% to 0.5% |
| Lanol ™ 99: | 2% |
| sweet almond oil: | 0.5% |
| water: | qs 100% |
| composition 2: | 3% |
| Sepicide ™ HB: | 0.3% |
| Sepicide ™ CI: | 0.2% |
| fragrance: | 0.4% |

EXAMPLE 25

Cream with AHA for Sensitive Skin

Formula

| mixture of lauryl amino acids: | 0.1% to 5% |
| --- | --- |
| magnesium potassium aspartate: | 0.002% to 0.5% |
| Lanol ™ 99: | 2% |
| Montanov ™ 68: | 5.0% |

EXAMPLE 26

After-Sun Soothing Care

Formula

| | |
|---|---|
| mixture of lauryl amino acids: | 0.1% to 5% |
| magnesium potassium aspartate: | 0.002% to 0.5% |
| Lanol ™ 99: | 10.0% |
| water: | qs 100% |
| composition 4: | 2.50% |
| Sepicide ™ HB: | 0.3% |
| Sepicide ™ CI: | 0.2% |
| fragrance: | 0.4% |
| dye: | 0.03% |

-continued

| | |
|---|---|
| water: | qs 100% |
| composition 2: | 1.50% |
| gluconic acid: | 1.50% |
| triethanolamine: | 0.9% |
| Sepicide ™ HB: | 0.3% |
| Sepicide ™ CI: | 0.2% |
| fragrance: | 0.4% |

EXAMPLE 27

Makeup-Removing Milk

Formula

| | |
|---|---|
| Sepiperl ™ N: | 3% |
| Primol ™ 352: | 8.0% |
| sweet almond oil: | 2% |
| water: | qs 100% |
| composition 3: | 0.8% |
| preserving agent: | 0.2% |

EXAMPLE 28

Body Milk

Formula

| | |
|---|---|
| Sepiperl ™ N: | 3.5% |
| Lanol ™ 37T: | 8.0% |
| Solagum ™ L: | 0.05% |
| water: | qs 100% |
| benzophenone: | 2.0% |
| Dimethicone 350 cPs: | 0.05% |
| composition 5: | 0.8% |
| preserving agent: | 0.2% |
| fragrance: | 0.4% |

EXAMPLE 29

Fluid Emulsion at Alkaline pH

| | |
|---|---|
| Marcol ™ 82: | 5.0% |
| NaOH: | 10.0% |
| water: | qs 100% |
| composition 2: | 1.5% | composition 2: 1.5%

EXAMPLE 30

Fluid Foundation

Formula

| | |
|---|---|
| Simulsol ™ 165: | 5.0% |
| Lanol ™ 84D: | 8.0% |
| Lanol ™ 99: | 5.0% |
| water: | qs 100% |
| mineral fillers and pigments: | 10.0% |
| composition 3: | 1.2% |
| preserving agent: | 0.2% |
| fragrance: | 0.4% |

EXAMPLE 31

Antisun Milk

Formula

| | |
|---|---|
| Sepiperl ™ N: | 3.5% |
| Lanol ™ 37T: | 10.0% |
| Parsol ™ NOX: | 5.0% |
| Eusolex ™ 4360: | 2.0% |
| water: | qs 100% |
| composition 4: | 1.8% |
| preserving agent: | 0.2% |
| fragrance: | 0.4% |

EXAMPLE 32

Eye Contour Gel

Formula

| | |
|---|---|
| composition 3: | 2.0% |
| fragrance: | 0.06% |
| sodium pyrrolidinonecarboxylate: | 0.2% |
| Dow Corning ™ 245 Fluid: | 2.0% |
| water: | qs 100% |

EXAMPLE 33

Leave-in Care Composition

Formula

| | |
|---|---|
| composition 4: | 1.5% |
| fragrance: | qs |
| preserving agent: | qs |
| Dow Corning ™ X2 8360: | 5.0% |
| Dow Corning ™ Q2 1401: | 15.0% |
| water: | qs 100% |

EXAMPLE 34

Slimming Gel

| | |
|---|---|
| composition 5: | 5% |
| ethanol: | 30% |
| menthol: | 0.1% |
| caffeine: | 2.5% |
| extract of ruscus: | 2% |
| extract of ivy: | 2% |
| Sepicide ™ HB | 1% |
| water | qs 100% |

EXAMPLE 35

Alcohol-Free Soothing Aftershave Balm

Formula

| | | |
|---|---|---|
| A | Lipacide ™ PVB: | 1.0% |
| | Lanol ™ 99: | 2.0% |
| | sweet almond oil: | 0.5% |
| B | composition 3: | 3.5% |
| C | water: | qs 100% |
| D | fragrance: | 0.4% |
| | Sepicide ™ HB: | 0.4% |
| | Sepicide ™ CI: | 0.2% |

EXAMPLE 36

Refreshing Aftershave Gel

Formula

| | | |
|---|---|---|
| A | Lipacide ™ PVB: | 0.5% |
| | Lanol ™ 99: | 5.0% |
| | composition 2: | 2.5% |
| B | water: | qs 100% |
| C | Micropearl ™ LM: | 0.5% |
| | fragrance: | 0.2% |
| | Sepicide ™ HB: | 0.3% |
| | Sepicide ™ CI: | 0.2% |

EXAMPLE 37

Care for Greasy Skin

Formula

| | | |
|---|---|---|
| A | Micropearl ™ M310: | 1.0% |
| | composition 4: | 5.0% |
| | octyl isononanoate: | 4.0% |
| B | water: | qs 100% |
| C | Sepicontrol ™ A5: | 4.0% |
| | fragrance: | 0.1% |
| | Sepicide ™ HB: | 0.3% |
| | Sepicide ™ CI: | 0.2% |
| D | Capigel ™ 98: | 0.5% |
| | water: | 10% |

EXAMPLE 38

Cream with AHA

Formula

| | | |
|---|---|---|
| A | Montanov ™ 68: | 5.0% |
| | Lipacide ™ PVB: | 1.05% |
| | Lanol ™ 99: | 10.0% |
| B | water: | qs 100% |
| | gluconic acid: | 1.5% |
| | TEA (triethanolamine): | 0.9% |
| C | composition 5: | 1.5% |
| D | fragrance: | 0.4% |
| | Sepicide ™ HB: | 0.2% |
| | Sepicide ™ CI: | 0.4% |

EXAMPLE 39

Nongreasy Self-Tanning Product for the Face and Body

Formula

| | | |
|---|---|---|
| A | Lanol ™ 2681: | 3.0% |
| | composition 4: | 2.5% |
| B | water: | qs 100% |
| | dihydroxyacetone: | 3.0% |
| C | fragrance: | 0.2% |
| | Sepicide ™ HB: | 0.8% |
| | sodium hydroxide: | qs pH = 5% |

EXAMPLE 40

Antisun Milk with Monoi Oil

Formula

| | | |
|---|---|---|
| A | monoi oil: | 10% |
| | Lipacide ™ PVB: | 0.5% |
| | composition 2: | 2.2% |
| B | water: | qs 100% |
| C | fragrance: | 0.1% |
| | Sepicide ™ HB: | 0.3% |

-continued

| | | |
|---|---|---|
| | Sepicide ™ CI: | 0.1% |
| | Parsol ™ MCX: | 4.0% |

EXAMPLE 41

Facial Antisun Care

Formula

| | | |
|---|---|---|
| A | DC ™ 1501: | 4.0% |
| | composition 3: | 3.5% |
| B | water: | qs 100% |
| C | fragrance: | 0.1% |
| | Sepicide ™ HB: | 0.3% |
| | Sepicide ™ CI: | 0.21% |
| | octyl methoxycinnamate: | 5.0% |
| | titanium mica: | 2.0% |
| | lactic acid: | qs ph = 6.5 |

EXAMPLE 42

No-Sun Tanning Emulsion

Formula

| | | |
|---|---|---|
| A | Lanol ™ 99: | 15% |
| | Montanov ™ 68: | 5.0% |
| | octyl para-methoxycinnamate: | 3.0% |
| B | water: | qs 100% |
| | dihydroxyacetone: | 5.0% |
| | monosodium phosphate: | 0.2% |
| C | composition 4: | 0.5% |
| D | fragrance: | 0.3% |
| | Sepicide ™ HB: | 0.8% |
| | sodium hydroxide: | qs pH = 5 |

EXAMPLE 43

Gloss Gel

| | |
|---|---|
| composition 5: | 1.5% |
| volatile silicone: | 25% |
| monopropylene glycol: | 25% |
| demineralized water: | 10% |
| glycerol: | qs 100% |

EXAMPLE 44

Slimming Gel

| | |
|---|---|
| composition 4: | 1.5% |
| Lanol ™ 99: | 2% |
| caffeine: | 5% |
| ethanol: | 40% |
| Micropearl ™ LM: | 2% |

-continued

| | |
|---|---|
| demineralized water: | qs 100% |
| preserving agent, fragrance: | qs |

EXAMPLE 45

Makeup-Removing Milk

| | |
|---|---|
| Simulsol ™ 165: | 4% |
| Montanov ™ 202: | 1% |
| triglyceride caprylate-caprate: | 15% |
| Pecosil ™ DCT: | 1% |
| demineralized water: | qs |
| Capigel ™ 98: | 0.5% |
| composition 5: | 1% |
| Proteol ™ Oat: | 2% |
| sodium hydroxide: | qs pH = 7 |

EXAMPLE 46

Restructuring "Rinse-Off" Cream Mask for Stressed and Embrittled Hair

Formula

| | |
|---|---|
| Keltrol ™ T: | 0.5% |
| Pecosil ™ SPP50: | 0.75% |
| N-Cocoyl amino acids: | 0.70% |
| butylene glycol: | 3.0% |
| composition 1: | 3.0% |
| Montanov ™ 82: | 3.0% |
| jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| fragrance: | 0.2% |
| water: | qs 100% |

EXAMPLE 47

Antisun Cream

| | |
|---|---|
| Simulsol ™ 165: | 3% |
| Montanov ™ 202: | 2% |
| C12-C15 benzoate: | 8% |
| Pecosil ™ PS 100: | 2% |
| dimethicone: | 2% |
| Dow Corning ™ 345: | 5% |
| octyl para-methoxycinnamate: | 6% |
| benzophenone-3: | 4% |
| titanium oxide: | 8% |
| Ketrol ™ T: | 0.2% |
| butylene glycol: | 5% |
| demineralized water: | qs 100% |
| composition 2: | 1.5% |
| preserving agent, fragrance: | qs |

EXAMPLE 48

Care Gel for Combination Skin

| | |
|---|---|
| composition 3: | 4% |
| plant squalane: | 5% |
| dimethicone: | 1.5% |
| Sepicontrol ™ A5: | 4% |
| Keltrol ™ T: | 0.3% |
| water: | qs 100% |
| preserving agent, fragrance: | |

EXAMPLE 49

Care Lotion

| | |
|---|---|
| butylene glycol: | 3.0% |
| composition 6: | 3% |
| Simulsol ™ 1293: | 3.0% |
| lactic acid: | qs pH = 6 |
| Sepicide ™ HB: | 0.2% |
| Sepicide ™ CI: | 0.3% |
| fragrance: | 0.3% |
| water: | qs 100% |

EXAMPLE 50

Protective, Relaxing Shampoo

| | |
|---|---|
| Amonyl ™ 675 SB: | 5.0% |
| 28% sodium lauryl ether sulfate: | 35.0% |
| composition 6: | 3.0% |
| Sepicide ™ HB: | 0.5% |
| Sepicide ™ CI: | 0.3% |
| sodium hydroxide: | qs ph = 7.2 |
| fragrance: | 0.3% |
| dye (FDC Blue 1/Yellow 5): | qs |
| water: | qs 100% |

EXAMPLE 51

"Leave-on" Protective Product: Antistress Haircare

| | |
|---|---|
| Keltrol ™ T: | 0.5% |
| mixture of cocoyl amino acids: | 3.0% |
| butylene glycol: | 5.0% |
| DC 1501: | 5.0% |
| composition 1: | 4.0% |
| Sepicide ™ HB: | 0.5% |
| Sepicide ™ CI: | 0.3% |
| fragrance: | 0.3% |
| water: | qs 100 |

EXAMPLE 52

Cream with Vitamins

| | |
|---|---|
| Simulsol ™ 165: | 5% |
| Montanov ™ 202: | 1% |
| caprylic/capric triglycerides: | 20% |
| vitamin A palmitate: | 0.2% |
| vitamin E acetate: | 1% |
| Micropearl ™ M305: | 1.5% |
| composition 1: | 2% |
| water: | qs 100% |
| preserving agent, fragrance: | qs |

EXAMPLE 53

Care Cream

| | |
|---|---|
| Dow Corning ™ 345: | 10% |
| composition 1 | 0.8% |
| Montanov ™ 68: | 2% |
| stearyl alcohol: | 1% |
| stearic alcohol: | 0.5% |
| preserving agent: | 0.65% |
| lysine: | 0.025% |
| EDTA (disodium salt): | 0.05% |
| Keltrol ™ T: | 0.2% |
| glycerol: | 3% |
| water: | qs 100% |

EXAMPLE 54

Aftershave Balm

Formula

| | | |
|---|---|---|
| A | composition 3: | 1.5% |
|   | water: | qs 100% |
| B | Micropearl ™ M100: | 5.0% |
|   | Sepicide ™ CI: | 0.50% |
|   | fragrance: | 0.20% |
|   | 95° ethanol: | 10.0% |

Procedure
Add B to A.

EXAMPLE 55

Satin Body Emulsion

Formula

| | | |
|---|---|---|
| A | Simulsol ™ 165: | 5.0% |
|   | Lanol ™ 1688: | 8.50% |
|   | shea butter: | 2% |
|   | liquid paraffin: | 6.5% |
|   | Lanol ™ 14M: | 3% |
|   | Lanol ™ S: | 0.6% |
| B | water: | 66.2% |
| C | Micropearl ™ M100: | 5% |

| | -continued | |
|---|---|---|
| D | composition 5: | 3% |
| E | Sepicide ™ CI: | 0.3% |
| | Sepicide ™ HB: | 0.5% |
| | Aquaxyl ™: | 3% |
| | fragrance: | 0.20% |
| | vitamin E acetate: | 0.20% |
| | sodium pyrrolidinonecarboxylate: | 1% |

Procedure

Add C to B, emulsify B in A at 70° C., then add D at 60° C., then E at 30° C.

EXAMPLE 56

O/W Cream

Formula

| A | Simulsol ™ 165: | 5.0% |
|---|---|---|
| | Lanol ™ 1688: | 20.0% |
| | Lanol ™ P: | 1.0% |
| B | water: | qs 100% |
| C | composition 2: | 2.50% |
| D | Sepicide ™ CI: | 0.20% |
| | Sepicide ™ HB: | 0.30% |

Procedure

Introduce B into A at about 75° C.; add C at about 60° C., then D at about 45° C.

EXAMPLE 57

Nongreasy Antisun Gel

Formula

| A | composition 7: | 3.00% |
|---|---|---|
| | water: | 30% |
| B | Sepicide ™ CI: | 0.20% |
| | Sepicide ™ HB: | 0.30% |
| | fragrance: | 0.10% |
| C | dye: | qs |
| | water: | 30% |
| D | Micropearl ™ M100: | 3.00% |
| | water: | qs 100% |
| E | silicone oil: | 2.0% |
| | Parsol ™ MCX: | 5.00% |

Procedure

Introduce B into A; add C, then D, then E.

EXAMPLE 58

Antisun Milk

Formula

| A | Montanov ™ S: | 3.0% |
|---|---|---|
| | sesameseed oil: | 5.0% |
| | Parsol ™ MCX: | 5.0% |
| | λ-Carrageenan: | 0.10% |
| B | water: | qs 100% |
| C | composition 1: | 0.80% |

| | -continued | |
|---|---|---|
| D | fragrance: | qs |
| | preserving agent: | qs |

Procedure

Emulsify B in A at 75° C., then add C at about 60° C., then D at about 30° C. and adjust the pH if necessary.

EXAMPLE 59

Massage Gel

Formula

| A | composition 8: | 3.5% |
|---|---|---|
| | water: | 20.0% |
| B | dye: | 2 drops/100 g |
| | water: | qs |
| C | alcohol: | 10% |
| | menthol: | 0.10% |
| D | silicone oil: | 5.0% |

Procedure

Add B to A, then add C to the mixture, then D.

EXAMPLE 60

Moisturizing and Matting Foundation

Formula

| A | water: | 20.0% |
|---|---|---|
| | butylene glycol: | 4.0% |
| | PEG-400: | 4.0% |
| | Pecosil ™ PS100: | 1.0% |
| | NaOH: | qs pH = 9 |
| | titanium dioxide: | 7.0% |
| | talc: | 2.0% |
| | yellow iron oxide: | 0.8% |
| | red iron oxide: | 0.3% |
| | black iron oxide: | 0.05% |
| B | Lanol ™ 99: | 8% |
| | caprylic/capric triglyceride: | 8% |
| | Montanov ™ 202: | 5.00% |
| C | water: | qs 100% |
| | Micropearl ™ M305: | 2.0% |
| | tetrasodium EDTA: | 0.05% |
| D | Down Corning ™ 345: | 4.0% |
| | xanthan gum: | 0.2% |
| | composition 5: | 0.8% |
| E | Sepicide ™ HB: | 0.5% |
| | Sepicide CI: | 0.3% |
| | fragrance: | 0.2% |

Procedure

Prepare mixtures B+D and A+C at 80° C., then mix together and emulsify.

EXAMPLE 61

Radiance Gel

Formula

| | | | |
|---|---|---|---|
| A | composition 5: | 4% | |
| | water: | 30% | |
| B | Elastin HPM: | 5.0% | |
| C | Micropearl ™ M100: | 3% | |
| | water: | 5% | |
| D | Sepicide ™ CI: | 0.2% | |
| | Sepicide ™ HB: | 0.3% | |
| | fragrance: | 0.06% | |
| | 50% sodium pyrrolidinonecarboxylate: | 1% | |
| | water: | qs 100% | |

Procedure

Prepare A; add B, then C, then D.

EXAMPLE 62

Body Milk

Formula

| | |
|---|---|
| Montanov ™ S: | 3.5% |
| Lanol ™ 37T: | 8.0% |
| Solagum ™ L: | 0.05% |
| water: | qs 100% |
| benzophenone-3: | 2.0% |
| Dimethicone 350 cPs: | 0.05% |
| composition 4: | 0.8% |
| preserving agent: | 0.2% |
| fragrance: | 0.4% |

EXAMPLE 63

Makeup-Removing Emulsion with Sweet Almond Oil

Formula

| | |
|---|---|
| Montanov ™ 68: | 5% |
| sweet almond oil: | 5% |
| water: | qs 100% |
| composition 3: | 0.3% |
| glycerol: | 5% |
| preserving agent: | 0.2% |
| fragrance: | 0.3% |

EXAMPLE 64

Moisturizing Cream for Greasy Skin

Formula

| | |
|---|---|
| Montanov ™ 68: | 5% |
| cetylstearyl octanoate: | 8% |
| octyl palmitate: | 2% |
| water: | qs 100% |
| composition 3: | 0.6% |
| Micropearl ™ M100: | 3.0% |
| mucopolysaccharides: | 5% |
| Sepicide ™ HB: | 0.8% |
| fragrance: | 0.3% |

EXAMPLE 65

Alcohol-Free Soothing Aftershave Balm

Formula

| | | |
|---|---|---|
| A | Lipacide ™ PVB: | 1.0% |
| | Lanol ™ 99: | 2.0% |
| | sweet almond oil: | 0.5% |
| B | composition 1: | 3.5% |
| C | water: | qs 100% |
| D | fragrance: | 0.4% |
| | Sepicide ™ HB: | 0.4% |
| | Sepicide ™ CI: | 0.2% |

EXAMPLE 66

Cream with AHA for Sensitive Skin

| | |
|---|---|
| mixture of lauryl amino acids: | 0.1% to 5% |
| magnesium potassium aspartate: | 0.002% to 0.5% |
| Lanol ™ 99: | 2% |
| Montanov ™ 68: | 5.0% |
| water: | qs 100% |
| composition 4: | 1.50% |
| gluconic acid: | 1.50% |
| triethylamine: | 0.9% |
| Sepicide ™ HB: | 0.3% |
| Sepicide ™ CI: | 0.2% |
| fragrance: | 0.4% |

EXAMPLE 67

After-Sun Soothing Care

| | |
|---|---|
| mixture of lauryl amino acids: | 0.1% to 5% |
| magnesium potassium aspartate: | 0.002% to 0.5% |
| Lanol ™ 99: | 10.0% |
| water: | qs 100% |
| composition 2: | 2.50% |
| Sepicide ™ HB: | 0.3% |
| Sepicide ™ CI: | 0.2% |
| fragrance: | 0.4% |
| dye: | 0.03% |

EXAMPLE 68

Makeup-Removing Milk

| | |
|---|---|
| Sepiperl ™ N: | 3% |
| Primol ™ 352: | 8.0% |
| sweet almond oil: | 2% |
| water: | qs 100% |
| composition 5: | 0.8% |
| preserving agent: | 0.2% |

EXAMPLE 69

Fluid Emulsion at Alkaline pH

| | |
|---|---|
| Marcol ™ 82: | 5.0% |
| NaOH: | 10.0% |
| water: | qs 100% |
| composition 4: | 1.5% |

EXAMPLE 70

Fluid Foundation

| | |
|---|---|
| Simulsol ™ 165: | 5.0% |
| Lanol ™ 84D: | 8.0% |
| Lanol ™ 99: | 5.0% |
| water: | qs 100% |
| mineral fillers and pigments: | 10.0% |
| composition 5: | 1.2% |
| preserving agent: | 0.2% |
| fragrance: | 0.4% |

EXAMPLE 71

Antisun Milk

| | |
|---|---|
| Sepiperl ™ N: | 3.5% |
| Lanol ™ 37T: | 10.0% |
| Parsol ™ NOX: | 5.0% |
| Eusolex ™ 4360: | 2.0% |
| water: | qs 100% |
| composition 1: | 1.8% |
| preserving agent: | 0.2% |
| fragrance: | 0.4% |

EXAMPLE 72

Eye Contour Gel

| | |
|---|---|
| composition 2: | 2.0% |
| fragrance: | 0.06% |
| sodium pyrrolidinonecarboxylate: | 0.2% |
| Dow Corning ™ 245 Fluid: | 2.0% |
| water: | qs 100% |

EXAMPLE 73

Leave-in Care Composition

| | |
|---|---|
| composition 3: | 1.5% |
| fragrance: | qs |
| preserving agent: | qs |
| Dow Corning ™ X2 8360: | 5.0% |
| Dow Corning ™ Q2 1401: | 15.0% |
| water: | qs 100% |

EXAMPLE 74

Slimming Gel

| | |
|---|---|
| composition 6: | 5% |
| ethanol: | 30% |
| menthol: | 0.1% |
| caffeine: | 2.5% |
| extract of ruscus: | 2% |
| extract of ivy: | 2% |
| Sepicide ™ HB: | 1% |
| water | qs 100% |

EXAMPLE 75

Ultra-Natural Tinted Cream Gel

Formula

| | | |
|---|---|---|
| A | water: | 10.0% |
| | butylene glycol: | 4.0% |
| | PEG-400: | 4.0% |
| | Pecosil ™ PS100: | 1.5% |
| | NaOH: | qs pH = 7 |
| | titanium dioxide: | 2.0% |
| | yellow iron oxide: | 0.8% |
| | red iron oxide: | 0.3% |
| | black iron oxide: | 0.05% |
| B | Lanol ™ 99: | 4.0% |
| | caprylic/capric triglyceride: | 4.0% |
| | Sepifeel ™ One: | 1.0% |
| | composition 5: | 3.0% |
| C | water: | qs 100% |
| | Micropearl ™ M305: | 2.0% |
| | tetrasodium EDTA: | 0.05% |
| | Dow Corning ™ 245 Fluid: | 4.0% |
| D | Sepicide ™ HB: | 0.5% |
| | Sepicide CI: | 0.3% |
| | fragrance: | 0.2% |

Procedure

Prepare the mixture B+C, then add A, then D.

EXAMPLE 76

Care for Greasy Skin

Formula

| | | |
|---|---|---|
| A | Micropearl ™ M310: | 1.0% |
| | composition 5: | 5.0% |
| | octyl isononanoate: | 4.0% |
| B | water: | qs 100% |
| C | Sepicontrol ™ A5: | 4.0% |
| | fragrance: | 0.1% |
| | Sepicide ™ HB: | 0.3% |
| | Sepicide ™ CI: | 0.2% |
| D | Capigel ™ 98: | 0.5% |
| | water: | 10% |

EXAMPLE 77

Cream with AHA

Formula

| | | |
|---|---|---|
| A | Montanov ™ 68: | 5.0% |
| | Lipacide ™ PVB: | 1.05% |
| | Lanol ™ 99: | 10.0% |
| B | water: | qs 100% |
| | gluconic acid: | 1.5% |
| | TEA (triethanolamine): | 0.9% |
| C | composition 4: | 1.5% |
| D | fragrance: | 0.4% |
| | Sepicide ™ HB: | 0.2% |
| | Sepicide ™ CI: | 0.4% |

EXAMPLE 78

Nongreasy Self-Tanning Product for the Face and Body

Formula

| | | |
|---|---|---|
| A | Lanol ™ 2681: | 3.0% |
| | composition 3: | 2.5% |
| B | water: | qs 100% |
| | dihydroxyacetone: | 3.0% |
| C | fragrance: | 0.2% |
| | Sepicide ™ HB: | 0.8% |
| | sodium hydroxide: | qs pH = 5% |

EXAMPLE 79

Antisun Milk with Monoi Oil

Formula

| | | |
|---|---|---|
| A | monoi oil: | 10% |
| | Lipacide ™ PVB: | 0.5% |
| | composition 7: | 2.2% |
| B | water: | qs 100% |
| C | fragrance: | 0.1% |
| | Sepicide ™ HB: | 0.3% |

-continued

| | |
|---|---|
| Sepicide ™ CI: | 0.1% |
| Parsol ™ MCX: | 4.0% |

EXAMPLE 80

Facial Antisun Care

Formula

| | | |
|---|---|---|
| A | DC ™ 1501: | 4.0% |
| | composition 5: | 3.5% |
| B | water: | qs 100% |
| C | fragrance: | 0.1% |
| | Sepicide ™ HB: | 0.3% |
| | Sepicide ™ CI: | 0.21% |
| | Parsol ™ MCX: | 5.0% |
| | titanium mica: | 2.0% |
| | lactic acid: | qs ph = 6.5 |

EXAMPLE 81

No-Sun Tanning Emulsion

Formula

| | | |
|---|---|---|
| A | Lanol ™ 99: | 15% |
| | Montanov ™ 68: | 5.0% |
| | Parsol ™ MCX: | 3.0% |
| B | water: | qs 100% |
| | dihydroxyacetone: | 5.0% |
| | monosodium phosphate: | 0.2% |
| C | composition 1: | 0.5% |
| D | fragrance: | 0.3% |
| | Sepicide ™ HB: | 0.8% |
| | NaOH: | qs pH = 5 |

EXAMPLE 82

Care Cream

| | |
|---|---|
| Dow Corning ™ 345: | 10% |
| composition 8: | 0.8% |
| Montanov ™ 68: | 4.5% |
| preserving agent: | 0.65% |
| lysine: | 0.025% |
| EDTA (disodium salt): | 0.05% |
| Keltrol ™ T: | 0.2% |
| glycerol: | 3% |
| water: | qs 100% |

EXAMPLE 83

Care Cream

| | |
|---|---|
| Dow Corning ™ 345: | 10% |
| composition 3: | 0.8% |

-continued

|   |   |   |
|---|---|---|
| | Montanov ™ 68: | 4.5% |
| | perfluoropolymethyl isopropyl ether: | 0.5% |
| | preserving agent: | 0.65% |
| | lysine: | 0.025% |
| | EDTA (disodium salt): | 0.05% |
| | Pemulen ™ TR: | 0.2% |
| | glycerol: | 3% |
| | water: | qs 100% | water: qs 100%

EXAMPLE 84

Body Milk

Formula

|   |   |   |
|---|---|---|
| A | Simulsol ™ 165: | 5.0% |
| | Lanol ™ 1688: | 12.0% |
| | Lanol ™ 14 M: | 2.0% |
| | cetyl alcohol: | 0.3% |
| | Schercemol ™ OP: | 3% |
| B | water: | qs 100% |
| C | composition 4: | 0.35% |
| D | Sepicide ™ CI: | 0.2% |
| | Sepicide ™ HB: | 0.5% |
| | fragrance: | 0.20% |

Procedure

Emulsify B in A at about 75° C.; add C at about 60° C. and then D at about 30° C.

EXAMPLE 85

Massage Care Gel

Formula

|   |   |   |
|---|---|---|
| A | composition 5: | 3.00% |
| | water: | 30% |
| B | Sepicide ™ CI: | 0.20% |
| | Sepicide ™ HB: | 0.30% |
| | fragrance: | 0.05% |
| C | dye: | qs |
| | water: | qs 100% |
| D | Micropearl ™ SQL: | 5.0% |
| | Lanol ™ 1688: | 2% |

Procedure

Prepare A; add B, then C, then D.

EXAMPLE 86

Body Milk

Formula

|   |   |   |
|---|---|---|
| A | Sepiperl ™ N: | 3.0% |
| | glyceryl triheptonate: | 10.0% |
| B | water: | qs 100% |

|   |   |   |
|---|---|---|
| C | composition 4: | 1.0% |
| D | fragrance: | qs |
| | preserving agent: | qs |

Procedure

Melt A at about 75° C. Emulsify B in A at 75° C. then add C at about 60° C., then D.

EXAMPLE 87

Alcohol-Free Soothing Aftershave Balm

|   |   |
|---|---|
| mixture of lauryl amino acids: | 0.1% to 5% |
| magnesium potassium aspartate: | 0.002% to 0.5% |
| Lanol ™ 99: | 2% |
| sweet almond oil: | 0.5% |
| water: | qs 100% |
| composition 3: | 3% |
| Sepicide ™ HB: | 0.3% |
| Sepicide ™ CI: | 0.2% |
| fragrance: | 0.4% |

EXAMPLE 88

Body Milk

|   |   |
|---|---|
| Sepiperl ™ N: | 3.5% |
| Lanol ™ 37T: | 8.0% |
| Solagum ™ L: | 0.05% |
| water: | qs 100% |
| benzophenone-3: | 2.0% |
| Dimethicone 350 cPs: | 0.05% |
| composition 2: | 0.8% |
| preserving agent: | 0.2% |
| fragrance: | 0.4% |

EXAMPLE 89

Alcohol-Free Soothing Aftershave Balm

Formula

|   |   |   |
|---|---|---|
| A | Lipacide ™ PVB: | 1.0% |
| | Lanol ™ 99: | 2.0% |
| | sweet almond oil: | 0.5% |
| B | composition 1: | 3.5% |
| C | water: | qs 100% |
| D | fragrance: | 0.4% |
| | Sepicide ™ HB: | 0.4% |
| | Sepicide ™ CI: | 0.2% |

EXAMPLE 90

Refreshing Aftershave Gel

Formula

| | | |
|---|---|---|
| A | Lipacide ™ PVB: | 0.5% |
| | Lanol ™ 99: | 5.0% |
| | composition 3: | 2.5% |
| B | water: | qs 100% |
| C | Micropearl ™ LM: | 0.5% |
| | fragrance: | 0.2% |
| | Sepicide ™ HB: | 0.3% |
| | Sepicide ™ CI: | 0.2% |

EXAMPLE 91

Cream with AHA

Formula

| | | |
|---|---|---|
| A | Montanov ™ 68: | 5.0% |
| | Lipacide ™ PVB: | 1.05% |
| | Lanol ™ 99: | 10.0% |
| B | water: | qs 100% |
| | gluconic acid: | 1.5% |
| | TEA (triethanolamine): | 0.9% |
| C | composition 3: | 1.5% |
| D | fragrance: | 0.4% |
| | Sepicide ™ HB: | 0.2% |
| | Sepicide ™ CI: | 0.4% |

EXAMPLE 92

Gloss Gel

| | |
|---|---|
| composition 7: | 1.5% |
| volatile silicone: | 25% |
| monopropylene glycol: | 25% |
| demineralized water: | 10% |
| glycerol: | qs 100% |

EXAMPLE 93

Slimming Gel

| | |
|---|---|
| composition 6: | 1.5% |
| Lanol ™ 99: | 2% |
| caffeine: | 5% |
| ethanol: | 40% |
| Micropearl ™ LM: | 2% |
| demineralized water: | qs 100% |
| preserving agent, fragrance: | qs |

EXAMPLE 94

Makeup-Removing Milk

| | |
|---|---|
| Simulsol ™ 165: | 4% |
| Montanov ™ 202: | 1% |
| triglyceride caprylate-caprate: | 15% |
| Pecosil ™ DCT: | 1% |
| demineralized water: | qs |
| Capigel ™ 98: | 0.5% |
| composition 4: | 1% |
| Proteol ™ Oat: | 2% |
| sodium hydroxide: | qs pH = 7 |

EXAMPLE 95

Restructuring "Rinse-Off" Cream Mask for Stressed and Embrittled Hair

Formula

| | |
|---|---|
| Keltrol ™ T: | 0.5% |
| Pecosil ™ SPP50: | 0.75% |
| N-Cocoyl amino acids: | 0.70% |
| butylene glycol: | 3.0% |
| composition 1: | 3.0% |
| Montanov ™ 82: | 3.0% |
| jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| fragrance: | 0.2% |
| water: | qs 100% |

EXAMPLE 96

Antisun Cream

| | |
|---|---|
| Simulsol ™ 165: | 3% |
| Montanov ™ 202: | 2% |
| C12-C15 benzoate: | 8% |
| Pecosil ™ PS 100: | 2% |
| dimethicone: | 2% |
| Dow Corning ™ 345: | 5% |
| Parsol ™ MCX: | 6% |
| benzophenone-3: | 4% |
| titanium oxide: | 8% |
| Keltrol ™ T: | 0.2% |
| butylene glycol: | 5% |
| demineralized water: | qs 100% |
| composition 8: | 1.5% |
| preserving agent, fragrance: | qs |

EXAMPLE 97

Care Gel for Combination Skin

| | |
|---|---|
| composition 3: | 4% |
| plant squalane: | 5% |
| dimethicone: | 1.5% |
| Sepicontrol ™ A5: | 4% |
| Keltrol ™ T: | 0.3% |
| water: | qs 100% |
| preserving agent, fragrance: | qs |

EXAMPLE 98

Care Lotion

| | |
|---|---|
| butylene glycol: | 3.0% |
| composition 4: | 3% |
| Simulsol ™ 1293: | 3.0% |
| lactic acid: | qs pH = 6 |
| Sepicide ™ HB: | 0.2% |
| Sepicide ™ CI: | 0.3% |
| fragrance: | 0.3% |
| water: | qs 100% |

EXAMPLE 99

Protective, Relaxing Shampoo

| | |
|---|---|
| Amonyl ™ 675 SB: | 5.0% |
| 28% sodium lauryl ether sulfate: | 35.0% |
| composition 6: | 3.0% |
| Sepicide ™ HB: | 0.5% |
| Sepicide ™ CI: | 0.3% |
| sodium hydroxide: | qs ph = 7.2 |
| fragrance: | 0.3% |
| dye (FDC Blue 1/Yellow 5): | qs |
| water: | qs 100% |

EXAMPLE 100

"Leave-on" Protective Product: Antistress Haircare

| | |
|---|---|
| Keltrol ™ T: | 0.5% |
| mixture of cocoyl amino acids: | 3.0% |
| butylene glycol: | 5.0% |
| DC 1501: | 5.0% |
| composition 1: | 4.0% |
| Sepicide ™ HB: | 0.5% |
| Sepicide ™ CI: | 0.3% |
| fragrance: | 0.3% |
| water: | qs 100 |

EXAMPLE 101

Cream with Vitamins

| | |
|---|---|
| Simulsol ™ 165: | 5% |
| Montanov ™ 202: | 1% |
| caprylic/capric triglycerides: | 20% |
| vitamin A palmitate: | 0.2% |
| vitamin E acetate: | 1% |
| Micropearl ™ M305: | 1.5% |
| composition 2: | 2% |
| water: | qs 100% |
| preserving agent, fragrance: | qs |

EXAMPLE 102

Antisun Gel

Formula

| | |
|---|---|
| composition 5: | 3.00% |
| Sepicide ™ CI: | 0.20% |
| Sepicide ™ HB: | 0.30% |
| fragrance: | 0.10% |
| dye: | qs |
| silica: | 3.00% |
| water: | qs 100% |
| silicone oil: | 2.0% |
| benzophenone-3: | 5.00% |

EXAMPLE 103

Lip Gloss

| | |
|---|---|
| composition 5: | 1.50% |
| Schercemol ™ TISC: | 15.00% |
| Vistanol ™ NPGC: | 15.00% |
| Candurin paprika: | 0.50% |
| Montanox ™ 80: | 1.00% |
| Antaron ™ V216: | 0.90% |
| apricot flavoring: | 0.20% |
| Sepicide ™ HB | 0.50% |
| C Maltidex ™ H16322 | qs 100% |

EXAMPLE 104

Sun Soil Pressed Powder

| | |
|---|---|
| composition 3: | 2.00% |
| Lanol ™ 99: | 12.00% |
| Sepiwhite ™ MSH | 1.00% |
| talc: | 33.00% |
| Micropearl ™ M310 | 3.00% |
| yellow iron oxide: | 0.80% |
| red iron oxide: | 0.30% |
| black iron oxide: | 0.05% |
| mica: | qs 100% |

EXAMPLE 105

Emulsion for Atopic-Prone Skin

| | |
|---|---|
| Arlacel ™ P135: | 2.00% |
| composition 6: | 1.00% |
| Lanol ™ 1688: | 14.00% |
| Primol ™ 352 | 8.00% |
| glycerol: | 5.00% |
| water: | qs 100% |
| magnesium sulfate: | 0.70% |
| Sepicide ™ HB: | 0.30% |
| Sepicide ™ CI: | 0.20% |
| Micropearl ™ M310: | 5.00% |

EXAMPLE 106

Soothing Antisun Care (Water-in-Silicone)

| | |
|---|---|
| composition 8: | 2.00% |
| DC5225C: | 20.00% |
| DC345: | 10.00% |
| Sepicalm ™ VG: | 3.00% |
| titanium dioxide MT100T: | 5.00% |
| zinc oxide Z-Cote HP1: | 5.00% |
| Sepicide ™ HB: | 0.30% |
| fragrance: | 0.05% |
| Sepicide ™ CI: | 0.20% |
| glycerol: | 5.00% |
| sodium chloride: | 2.00% |
| water: | qs 100% |

EXAMPLE 107

Multiphase Care

| | |
|---|---|
| composition 7: | 3.00% |
| C12-15 alkyl benzoate: | 25.00% |
| Aquaxyl ™: | 3.00% |
| Sepitonic ™ M3: | 1.00% |
| Sepicide ™ HB: | 0.50% |
| Sepicide ™ CI: | 0.30% |
| water: | qs 100% |

The definitions of the commercial products used in the examples are as follows:

SimulSol™ 1293 is hydrogenated and ethoxylated castor oil, with an ethoxylation index equal to 40, sold by the company SEPPIC.

Capigel™ 98 is a liquid thickener based on acrylate copolymer sold by the company SEPPIC.

Keltrol™ T is xanthan gum sold by the company Kelco.

Lanol™ 99 is isononyl isononanoate sold by the company SEPPIC.

DC1501 is a mixture of cyclopentasiloxane and dimethiconol sold by the company Dow Chemical.

Montanov™ 82 is an emulsifier based on cetearyl alcohol and cocoylglucoside.

Montanov™ 68 (cetearyl glucoside) is a self-emulsifying composition as described in WO 92/06778, sold by the company SEPPIC.

Micropearl™ M100 is an ultrafine powder with a very soft feel and a matting action, sold by the company Matsumo.

Sepicide™ CI, imidazolidine urea, is a preserving agent sold by the company SEPPIC.

Pemulen™ TR is an acrylic polymer sold by Goodrich.

Simulsol™ 165 is self-emulsifying glyceryl stearate sold by the company SEPPIC.

Lanol™ 1688 is an emollient ester with a nongreasy effect sold by the company SEPPIC.

Lanol™ 14M and Lanol® S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Aquaxyl™ is a moisturizer sold by the company SEPPIC.

Schercemol™ OP is an emollient ester with a nongreasy effect.

Lanol™ P is an additive with a stabilizing effect sold by the company SEPPIC.

Parsol™ MCX is octyl para-methoxycinnamate sold by the company Givaudan.

Sepiperl™ N is a pearlescent agent, sold by the company SEPPIC, based on a mixture of alkyl polyglucosides such as those described in WO 95/13863.

Micropearl™ SQL is a mixture of microparticles containing squalane, which is released by the action of massaging; it is sold by the company Matsumo.

Lanol™ 37T is glyceryl triheptanoate sold by the company SEPPIC.

Solagum™ L is a carrageenan sold by the company SEPPIC.

Marcol™ 82 is a liquid paraffin sold by the company Exxon.

Lanol™ 84D is dioctyl malate sold by the company SEPPIC.

Parsol NOX™ is a sunscreen sold by the company Givaudan.

Eusolex™ 4360 is a sunscreen sold by the company Merck.

Dow Corning™ 245 Fluid is cyclomethicone sold by the company Dow Corning.

Lipacide™ PVB is an acylated wheat protein hydrolyzate sold by the company SEPPIC.

Micropearl™ LM is a mixture of squalane, polymethyl methacrylate and menthol, sold by the company SEPPIC.

Sepicontrol™ A5 is a mixture of capryloyl glycine, sarcosine and extract of Cinnamon zylanicum, sold by the company SEPPIC, such as those described in international patent application PCT/FR98/01313 filed on 23 Jun. 1998.

Lanol™ 2681 is a mixture of coconut caprylate/caprate sold by the company SEPPIC.

Montanov™ 202 is an APG/fatty alcohol composition as described in WO 98/47610, sold by the company SEPPIC.

Proteol™ APL is a foaming surfactant sold by the company SEPPIC.

Schercemol™ TISC is an ester (triisostearyl citrate) sold by the company Scher.

Vistanol™ NPGC is an ester (neopentyl glycol dicaprate) sold by the company Sewa Kasei.

Antaron™ V216 is a synthetic polymer (PVP/hexadecene copolymer) distributed by the company Univar.

C Maltidex™ H16322 is a polyol (maltitol syrup) sold by the company Cerestar.

Sepiwhite™ MSH is a depigmenting active agent (undecylenoyl phenylalanine) sold by the company SEPPIC.

DC 345 is a cyclomethicone sold by the company Dow Corning.

DC 5225C is a mixture of cyclopentasiloxane and dimethicone copolyol sold by the company Dow Corning.

Sepicalm™ VG is a calmative active agent (sodium palmitoylproline) sold by the company SEPPIC.

MT100VT is a micronized titanium dioxide that has undergone a surface treatment (aluminum hydroxide/stearic acid) distributed by the company Unipex.

Z-Cote HP1 is a micronized zinc oxide that has undergone a surface treatment, distributed by Gattefosse.

Candurin paprika is a mixture of potassium aluminum silicate and iron oxide.

Monteine™ CA is a moisturizer sold by the company SEPPIC.

The invention claimed is:

1. A composition in the form of an inverse latex comprising:
   a) from 50% by weight to 80% of at least one linear, branched or crosslinked organic polymer (P),
   b) from 5% by weight to 10% of an emulsifying system ($S_1$) which is a water-in-oil (W/O) emulsion,
   c) from 5% by weight to 45% by weight of at least one oil, and
   d) from 0% to 5% of water,
   wherein from 0.01% to 10% in molar proportions of monomer units of said polymer P include at least one neutral monomer of formula (I'):

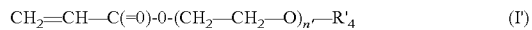
   $$CH_2=CH-C(=O)-O-(CH_2-CH_2-O)_{n'}-R'_4 \qquad (I')$$

radical $R'_4$ is an aliphatic radical selected from the group consisting of octyl, decyl, dodecyl, tetradecyl, hexadecyl, octadecyl, eicosyl, docosyl and tetracosyl radicals, and
   n' is a number between 4 and 25; or
   said polymer (P) is a copolymer in which each of the monomers, which are different from formula (I'), is independently of each other selected from the group consisting of a monomer containing a partially or totally salified strong acid function, a monomer containing a partially or totally salified weak acid function and from neutral a monomer.

2. The composition as defined in claim 1, in which from 0.05 mol % to 5 mol % of the monomer units that said polymer P comprises include at least one neutral monomer of formula (I').

3. The composition as defined in claim 1, wherein the polymer (P) is crosslinked with a diethylenic or polyethylenic compound in a molar proportion, expressed relative to the monomers used, of less than or equal to 0.25%.

4. The composition as defined in claim 3, wherein the crosslinking agent is selected from the group consisting of ethylene glycol dimethacrylate, diethylene glycol diacrylate, sodium diallyloxyacetate, ethylene glycol diacrylate, diallyl urea, triallylamine, trimethylolpropane triacrylate and methylenebis(acrylamide), or a mixture of these compounds.

5. The composition as defined in claim 1, wherein the monomer containing a strong acid function, which the polymer (P) comprises, is partially or totally salified 2-methyl-2-[(1-oxo-2-propenyl)amino]-1-propanesulfonic acid.

6. The composition as defined in claim 1, wherein the monomer containing a weak acid function, which the polymer (P) comprises, is selected from the group consisting of acrylic acid, methacrylic acid, itaconic acid, maleic acid and partially or totally salified 3-methyl-3-[(1-oxo-2-propenyl)amino]butanoic acid.

7. The composition as defined in claim 1, wherein the neutral monomer other than the compound of formula (I'), which the polymer (P) comprises, is selected from the group consisting of acrylamide, methacrylamide, diacetoneacrylamide, dimethylacrylamide, N-isopropylacrylamide, N-[2-hydroxy-1,1-bis(hydroxymethyl)ethyl]propenamide, (2-hydroxyethyl) acrylate, (2,3-dihydroxypropyl) acrylate, (2-hydroxyethyl) methacrylate, (2,3-dihydroxypropyl) methacrylate, and an ethoxylated derivative with a molecular weight of between 400 and 1000, of each of these esters, or vinylpyrrolidone.

8. The composition as defined in claim 1, in which the polymer (P) is selected from the group consisting of:
   crosslinked copolymers of acrylic acid partially salified in the form of the sodium salt or of the ammonium salt, of acrylamide and of tetraethoxylated lauryl acrylate;
   crosslinked copolymers of 2-methyl-2-[(1-oxo-2-propenyl)amino]-1-propanesulfonic acid partially salified in the form of the sodium salt, of acrylamide and of tetraethoxylated lauryl acryate;
   crosslinked copolymers of 2-methyl-2-[(1-oxo-2-propenyl)amino]-1-propanesulfonic acid and of acrylic acid, which are partially salified in the form of the sodium salt, and of tetraethoxylated lauryl acrylate;
   crosslinked copolymers of 2-methyl-2-[(1-oxo-2-propenyl)amino]-1-propanesulfonic acid partially salified in the form of the sodium salt, of 2-hydroxyethyl acrylate and of tetraethoxylated lauryl acrylate;
   crosslinked copolymers of 2-methyl-2-[(1-oxo-2-propenyl)amino]-1-propanesulfonic acid partially salified in the form of the sodium salt, and of tetraethoxylated lauryl acrylate;
   crosslinked copolymers of acrylic acid partially salified in the form of the ammonium salt or of the monoethanolamine salt, and of tetraethoxylated lauryl acrylate;
   crosslinked copolymers of acrylamide, of 2-methyl-2-[(1-oxo-2-propenyl)amino]-1-propanesulfonic acid and of acrylic acid, which are partially salified in the form of the sodium salt, and of tetraethoxylated lauryl acrylate; and
   copolymers of 2-methyl-2-[(1-oxo-2-propenyl)-amino]-1-propanesulfonic acid partially salified in the form of the sodium salt, of acrylamide, of vinylpyrrolidone and of tetraethoxylated lauryl acrylate.

9. The composition as defined in claim 1, comprising from 60% by weight to 70% by weight of polymer (P).

10. The composition as defined in claim 1, further comprising up to 5% of its weight of an emulsifying system ($S_2$) which is a water-in-oil (W/O) emulsion.

* * * * *